(12) United States Patent
Govari et al.

(10) Patent No.: US 11,426,126 B2
(45) Date of Patent: Aug. 30, 2022

(54) INDICATING ELECTRODE CONTACT

(71) Applicant: Biosense Webster (Israel) Ltd., Yokneam (IL)

(72) Inventors: Assaf Govari, Haifa (IL); Vadim Gliner, Haifa (IL); Uri Avni, Ram-on (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 156 days.

(21) Appl. No.: 16/421,416

(22) Filed: May 23, 2019

(65) Prior Publication Data

US 2020/0367829 A1  Nov. 26, 2020

(51) Int. Cl.
*A61B 5/00* (2006.01)
*A61B 5/287* (2021.01)
*A61B 5/339* (2021.01)

(52) U.S. Cl.
CPC ............ *A61B 5/6885* (2013.01); *A61B 5/287* (2021.01); *A61B 5/339* (2021.01); *A61B 5/6859* (2013.01); *A61B 5/7221* (2013.01); *A61B 2562/0209* (2013.01)

(58) Field of Classification Search
CPC ... A61B 5/6885; A61B 5/6859; A61B 5/7221; A61B 2562/0209
See application file for complete search history.

(56) References Cited

U.S. PATENT DOCUMENTS

| | | | |
|---|---|---|---|
| 5,078,714 | A | 1/1992 | Katims |
| 5,341,807 | A | 8/1994 | Nardella |
| 5,391,199 | A | 2/1995 | Ben-Haim |
| 5,447,529 | A | 9/1995 | Marchlinski et al. |
| 5,469,857 | A | 11/1995 | Laurent et al. |
| 5,662,108 | A | 9/1997 | Budd et al. |
| 5,673,704 | A | 10/1997 | Marchlinski et al. |
| 5,836,874 | A | 11/1998 | Swanson et al. |

(Continued)

FOREIGN PATENT DOCUMENTS

| | | |
|---|---|---|
| CA | 2285342 A1 | 10/1998 |
| WO | WO 1996/005768 A1 | 2/1996 |
| WO | WO 2019/018182 A1 | 1/2019 |

OTHER PUBLICATIONS

Partial European Search Report dated Oct. 9, 2020, Application No. EP 20 17 5998.

(Continued)

*Primary Examiner* — Paula J Stice
(74) *Attorney, Agent, or Firm* — Frost Brown Todd LLC

(57) ABSTRACT

In one embodiment, a medical system, includes a catheter to be inserted into a chamber of a heart of a living subject, and including catheter electrodes configured to contact tissue at respective locations within the chamber of the heart, a display, and processing circuitry to receive signals from the catheter, and in response to the signals assess a respective quality of contact of each of the catheter electrodes with the tissue in the heart, and render to the display respective intracardiac electrograms traces representing electrical activity in the tissue that is sensed by the catheter electrodes at the respective locations, while modifying a visual feature of at least some of the traces responsively to the respective quality of contact of the catheter electrodes with the tissue of the heart at the respective locations.

23 Claims, 6 Drawing Sheets

(56) References Cited

U.S. PATENT DOCUMENTS

| | | |
|---|---|---|
| 5,836,990 A | 11/1998 | Li |
| 5,891,095 A | 4/1999 | Eggers et al. |
| 5,935,079 A | 8/1999 | Swanson et al. |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,756,576 B2 | 7/2010 | Levin |
| 7,848,787 B2 | 12/2010 | Osadchy |
| 7,869,865 B2 | 1/2011 | Govari et al. |
| 9,168,004 B2 | 10/2015 | Gliner et al. |
| 2002/0006455 A1 | 1/2002 | Levine |
| 2003/0120150 A1 | 6/2003 | Govari |
| 2004/0068178 A1 | 4/2004 | Govari |
| 2007/0100332 A1 | 5/2007 | Paul et al. |
| 2009/0093806 A1 | 4/2009 | Govari et al. |
| 2009/0138007 A1 | 5/2009 | Govari et al. |
| 2009/0177111 A1 | 7/2009 | Miller et al. |
| 2009/0248014 A1 | 10/2009 | Shachar et al. |
| 2011/0313280 A1* | 12/2011 | Govari ................. A61B 5/6885 600/424 |
| 2013/0085416 A1 | 4/2013 | Mest |
| 2014/0180152 A1* | 6/2014 | Maskara ................. A61B 5/339 600/523 |
| 2014/0343427 A1 | 11/2014 | Fukunaga et al. |
| 2015/0216437 A1 | 8/2015 | Mihajlovic |
| 2018/0078300 A1 | 3/2018 | Paul et al. |
| 2018/0153437 A1* | 6/2018 | Schwartz ........... A61B 18/1492 |
| 2021/0145344 A1* | 5/2021 | Mangual-Soto ..... A61B 5/7221 |

OTHER PUBLICATIONS

European Search Report dated Oct. 9, 2020, Application No. EP 20 17 5998.

* cited by examiner

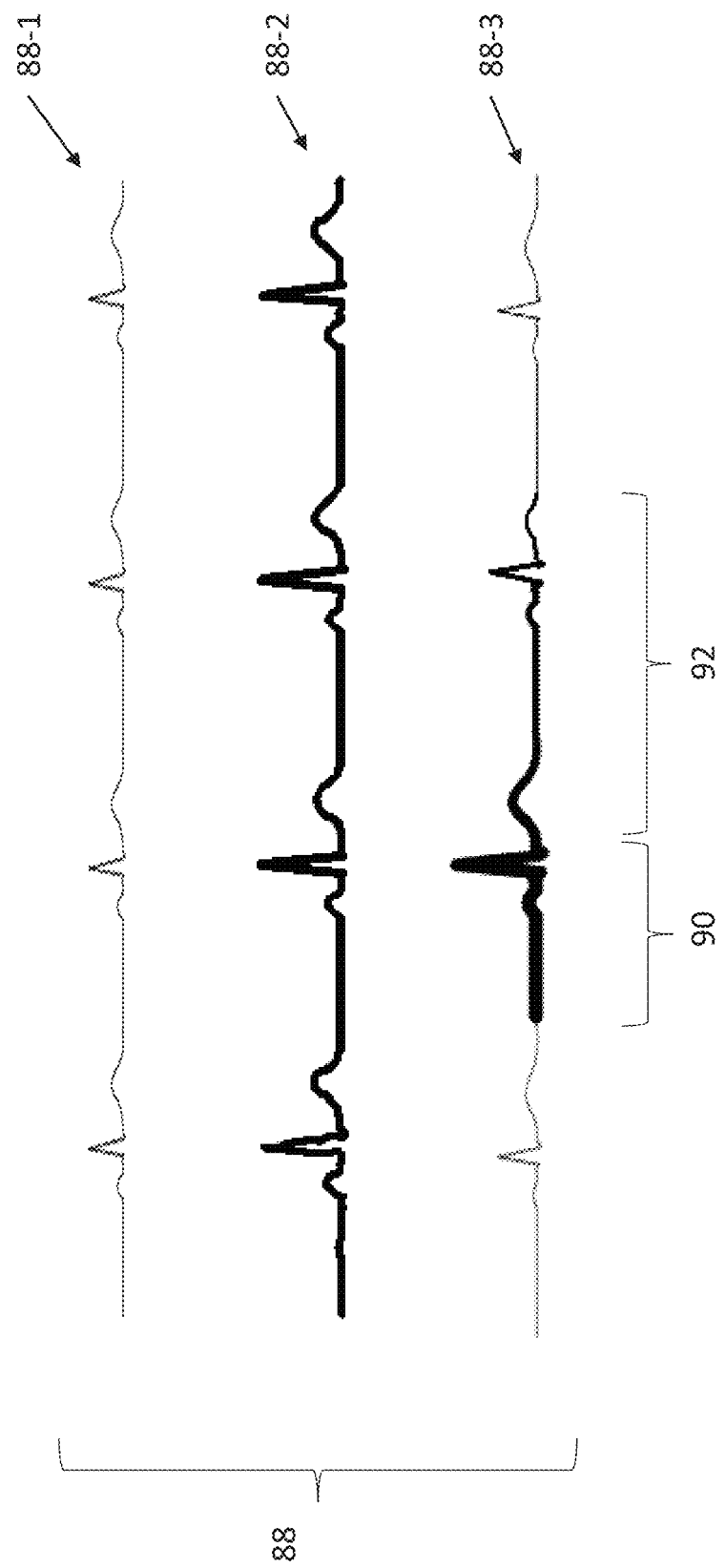

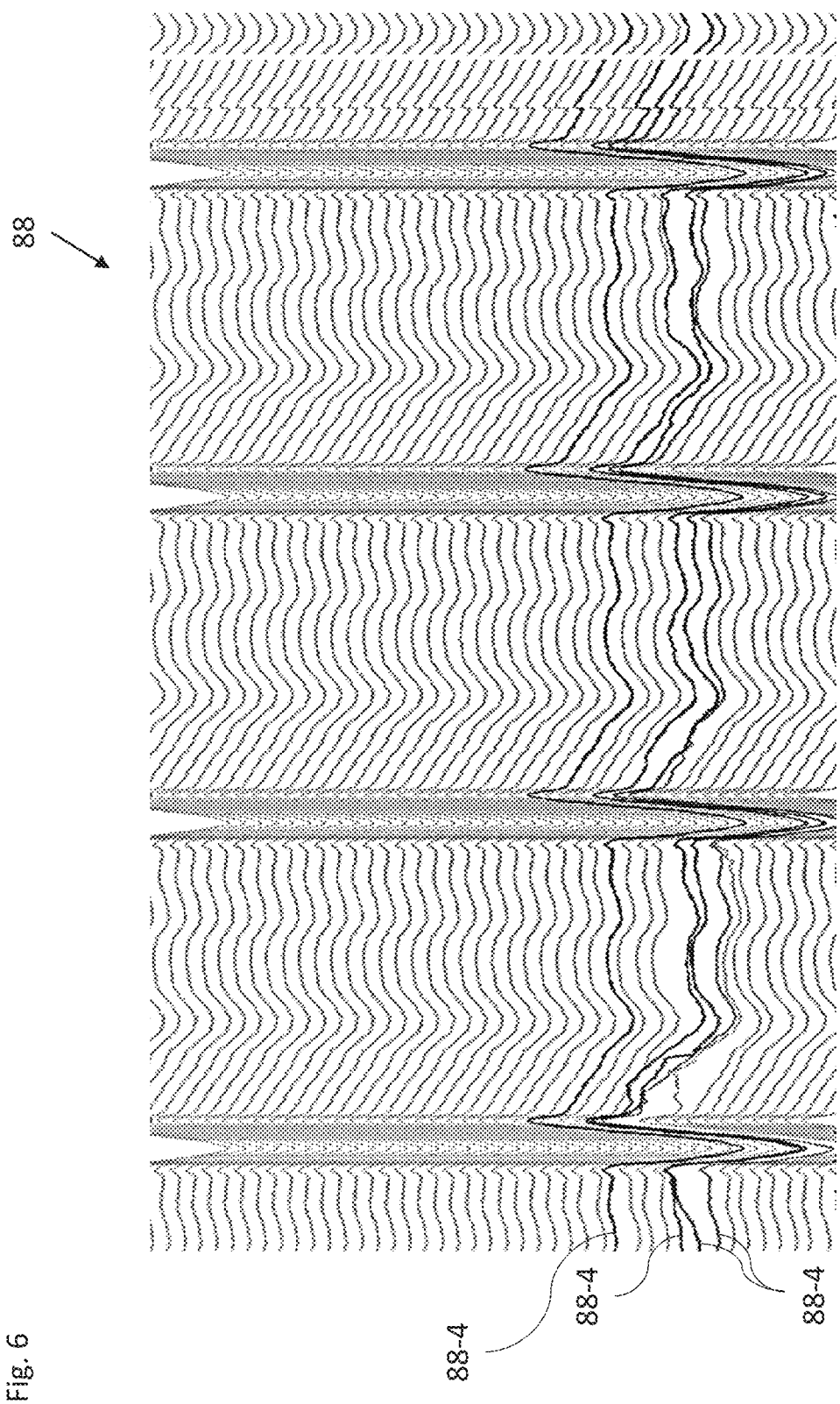

INDICATING ELECTRODE CONTACT

FIELD OF THE INVENTION

The present invention relates to medical systems, and in particular, but not exclusively to, catheter-based systems.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455, issued as U.S. Pat. No. 6,690,963 on Feb. 10, 2004; and 2003/0120150, issued as U.S. Pat. No. 7,729,742 on Jun. 1, 2010; and 2004/0068178, now abandoned, whose disclosures are all incorporated herein by reference. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied to the tip electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, issued as U.S. Pat. No. 8,021,361 on Sep. 20, 2011; 2009/0093806 issued as U.S. Pat. No. 8,357,152 on Jan. 22, 2013; and 2009/0138007, issued as U.S. Pat. No. 8,535,308 on Sep. 17, 2013, whose disclosures are incorporated herein by reference describe methods of sensing contact pressure between the distal tip of a catheter and tissue in a body cavity using a force sensor embedded in the catheter.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342. A number of these references, e.g., U.S. Pat. Nos. 5,935,079, 5,836,990, and 5,447,529 determine electrode-tissue contact by measuring the impedance between the tip electrode and a return electrode. As disclosed in the '529 patent, it is generally known than impedance through blood is generally lower that impedance through tissue. Accordingly, tissue contact has been detected by comparing the impedance values across a set of electrodes to premeasured impedance values when an electrode is known to be in contact with tissue and when it is known to be in contact only with blood.

U.S. Pat. No. 9,168,004 to Gliner, at al., which is herein incorporated by reference, describes using machine learning to determine catheter electrode contact. The '004 Patent describes cardiac catheterization being carried out by memorizing a designation of a contact state between an electrode of the probe and the heart wall as an in-contact state or an out-of-contact state, and making a series of determinations of an impedance phase angle of an electrical current passing through the electrode and another electrode, identifying maximum and minimum phase angles in the series, and defining a binary classifier adaptively as midway between the extremes. A test value is compared to the classifier as adjusted by a hysteresis factor, and a change in the contact state is reported when the test value exceeds or falls below the adjusted classifier.

US Patent Publication 2013/0085416, issued as U.S. Pat. No. 10,791,950 on Oct. 6, 2020, of Mest, which is herein incorporated by reference, describes a method for the in vivo re-calibration of a force sensing probe such as an electrophysiology catheter which provides for the generation of an auto zero zone. The distal tip of the catheter or other probe is placed in a body cavity within the patient. Verification that there is no tissue contact is made using electrocardiogram (ECG) or impedance data, fluoroscopy or other real-time imaging data and/or an electro-anatomical mapping system. Once verification that there is no tissue contact made, the system recalibrates the signal emanating from the force sensor setting it to correspond to a force reading of zero grams and this recalibrated baseline reading is used to generate and display force readings based on force sensor data.

SUMMARY

There is provided in accordance with an embodiment of the present disclosure, a medical system, including a catheter configured to be inserted into a chamber of a heart of a living subject, and including catheter electrodes configured to contact tissue at respective locations within the chamber of the heart, a display, and processing circuitry configured to receive signals from the catheter, and in response to the signals assess a respective quality of contact of each of the catheter electrodes with the tissue in the heart, and render to the display respective intracardiac electrograms (IEGM) traces representing electrical activity in the tissue that is sensed by the catheter electrodes at the respective locations, while modifying a visual feature of at least some of the traces responsively to the respective quality of contact of the catheter electrodes with the tissue of the heart at the respective locations.

Further in accordance with an embodiment of the present disclosure the processing circuitry is configured to increase a brightness of at least some of the traces responsively to the respective quality of contact of the catheter electrodes with the tissue of the heart at the respective locations.

Still further in accordance with an embodiment of the present disclosure the processing circuitry is configured to increase the brightness of the traces representing the electrical activity sensed by first ones of the catheter electrodes having a high quality of contact with the tissue relative to the traces representing the electrical activity sensed by second ones of the catheter electrodes having a lower quality of contact with the tissue.

Additionally, in accordance with an embodiment of the present disclosure the processing circuitry is configured to change a color of at least some of the traces responsively to the respective quality of contact of the catheter electrodes with the tissue of the heart at the respective locations.

Moreover in accordance with an embodiment of the present disclosure the processing circuitry is configured to change the color of the traces representing the electrical activity sensed by first ones of the catheter electrodes having a high quality of contact with the tissue relative to the traces representing the electrical activity sensed by second ones of the catheter electrodes having a lower quality of contact with the tissue.

Further in accordance with an embodiment of the present disclosure the processing circuitry is configured to modify the visual feature of the at least some traces representing the electrical activity sensed by ones of the catheter electrodes having a quality of contact with the tissue greater than a predefined threshold quality of contact.

Still further in accordance with an embodiment of the present disclosure the processing circuitry is configured to perform a first modification of the visual feature of one of the traces representing the electrical activity sensed by one of the catheter electrodes having a quality of contact with the tissue greater than the predefined threshold quality during a first time period, and perform a second modification of the visual feature of the one trace representing the electrical activity sensed by the one catheter electrode having a quality of contact with the tissue less than the predefined threshold quality during a second time period following the first time period.

Additionally, in accordance with an embodiment of the present disclosure the second modification of the visual feature changes as the second time period progresses.

Moreover, in accordance with an embodiment of the present disclosure the second modification of the visual feature includes the visual feature becoming dimmer as the second time period progresses.

Further in accordance with an embodiment of the present disclosure, the system includes body-surface electrodes configured to be applied to a skin surface of the living subject, wherein the processing circuitry is configured to measure an indication of electrical impedances between the body-surface electrodes and the catheter electrodes, and compute position coordinates of the catheter electrodes responsively to the indication of the electrical impedances.

Still further in accordance with an embodiment of the present disclosure the processing circuitry is configured to assess the respective quality of contact of each of the catheter electrodes with the tissue in the heart responsively to the indication of the electrical impedances.

There is also provided in accordance with another embodiment of the present disclosure a medical method, including receiving signals from a catheter configured to be inserted into a chamber of a heart of a living subject, and including catheter electrodes configured to contact tissue at respective locations within the chamber of the heart, in response to the signals, assessing a respective quality of contact of each of the catheter electrodes with the tissue in the heart, and rendering to a display respective intracardiac electrograms (IEGM) traces representing electrical activity in the tissue that is sensed by the catheter electrodes at the respective locations, while modifying a visual feature of at least some of the traces responsively to the respective quality of contact of the catheter electrodes with the tissue of the heart at the respective locations.

Additionally, in accordance with an embodiment of the present disclosure, the method includes increasing a brightness of at least some of the traces responsively to the respective quality of contact of the catheter electrodes with the tissue of the heart at the respective locations.

Moreover in accordance with an embodiment of the present disclosure the increasing includes increasing the brightness of the traces representing the electrical activity sensed by first ones of the catheter electrodes having a high quality of contact with the tissue relative to the traces representing the electrical activity sensed by second ones of the catheter electrodes having a lower quality of contact with the tissue.

Further in accordance with an embodiment of the present disclosure, the method includes changing a color of at least some of the traces responsively to the respective quality of contact of the catheter electrodes with the tissue of the heart at the respective locations.

Still further in accordance with an embodiment of the present disclosure the changing includes changing the color of the traces representing the electrical activity sensed by first ones of the catheter electrodes having a high quality of contact with the tissue relative to the traces representing the electrical activity sensed by second ones of the catheter electrodes having a lower quality of contact with the tissue.

Additionally, in accordance with an embodiment of the present disclosure the modifying includes modifying the visual feature of the at least some traces representing the electrical activity sensed by ones of the catheter electrodes having a quality of contact with the tissue greater than a predefined threshold quality of contact.

Moreover in accordance with an embodiment of the present disclosure, the method includes performing a first modification of the visual feature of one of the traces representing the electrical activity sensed by one of the catheter electrodes having a quality of contact with the tissue greater than the predefined threshold quality during a first time period, and performing a second modification of the visual feature of the one trace representing the electrical activity sensed by the one catheter electrode having a quality of contact with the tissue less than the predefined threshold quality during a second time period following the first time period.

Further in accordance with an embodiment of the present disclosure the second modification of the visual feature changes as the second time period progresses.

Still further in accordance with an embodiment of the present disclosure the second modification of the visual feature includes the visual feature becoming dimmer as the second time period progresses.

Additionally, in accordance with an embodiment of the present disclosure, the method includes measuring an indication of electrical impedances between body-surface electrodes, configured to be applied to a skin surface of the living subject, and the catheter electrodes, and computing position coordinates of the catheter electrodes responsively to the indication of the electrical impedances.

Moreover, in accordance with an embodiment of the present disclosure the assessing includes assessing the respective quality of contact of each of the catheter electrodes with the tissue in the heart responsively to the indication of the electrical impedances.

There is also provided in accordance with still another embodiment of the present disclosure a software product, including a non-transient computer-readable medium in which program instructions are stored, which instructions, when read by a central processing unit (CPU), cause the CPU to receive signals from a catheter configured to be inserted into a chamber of a heart of a living subject, and including catheter electrodes configured to contact tissue at respective locations within the chamber of the heart, in response to the signals, assess a respective quality of contact of each of the catheter electrodes with the tissue in the heart, and render to a display respective intracardiac electrograms (IEGM) traces representing electrical activity in the tissue that is sensed by the catheter electrodes at the respective locations, while modifying a visual feature of at least some of the traces responsively to the respective quality of contact of the catheter electrodes with the tissue of the heart at the respective locations.

BRIEF DESCRIPTION OF THE DRAWINGS

The present invention will be understood from the following detailed description, taken in conjunction with the drawings in which:

FIG. 5 is a schematic view of first exemplary intracardial electrogram (IEGM) traces prepared by the system of FIG. 1; and FIG. 6 is a schematic view of second exemplary intracardial electrogram (IEGM) traces prepared by the system of FIG. 1.

DESCRIPTION OF EXAMPLE EMBODIMENTS

Overview

Figure 1:
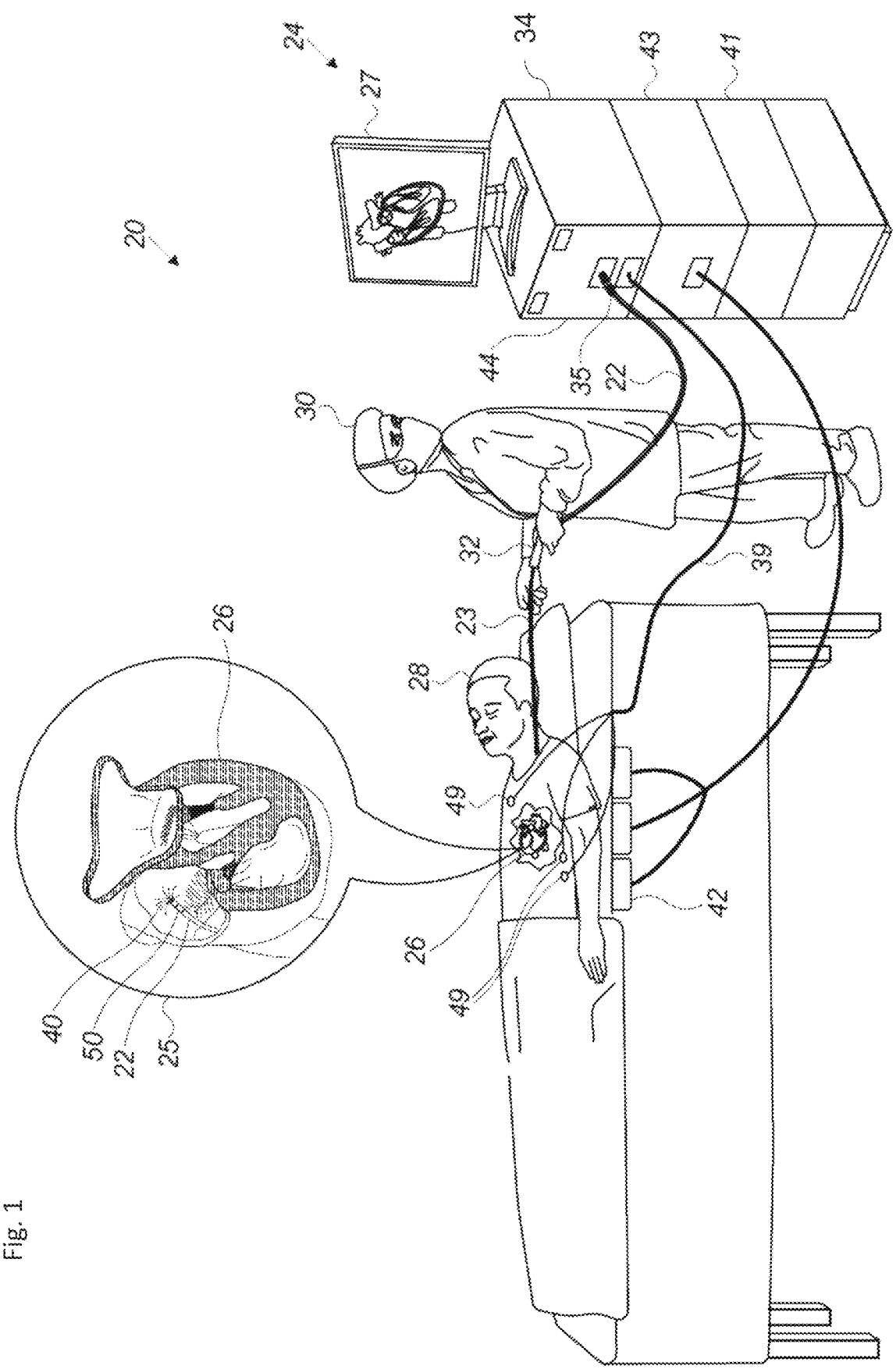
FIG. 1 is a schematic view of a medical procedure system constructed and operative in accordance with an embodiment of the present invention.

As mentioned previously, in a two-step procedure, mapping followed by ablation, electrical activity at points within the heart is typically sensed and measured by advancing a catheter containing one or more electrodes into the heart, and acquiring data at a multiplicity of points. These data are then utilized to select the target areas at which the ablation is to be performed.

In particular, the electrical activity is typically displayed as intracardial electrogram (IEGM) traces for analysis by a physician in order to find sources of arrhythmia. A catheter electrode, which is not in contact with tissue in the heart, generally measures some electrical signal from the heart tissue and a far field signal. When the catheter electrode is in contact with the heart tissue, the amplitude of the signal is mainly based on tissue conductivity, while the far field is minor. Therefore, the physician is generally interested in analyzing the IEGM traces of electrodes in contact with the tissue.

For focal catheters with one or two electrodes, a single IEGM trace is typically displayed for a physician to analyze. A physician can quickly determine based on the form of the signal whether the catheter electrode providing the signal is in contact with the tissue. However, multi-electrode catheters simultaneously capturing electrical activity from different tissue locations may provide data for a plurality of IEGM traces to be displayed at the same time on a single display. In some cases, the number of IEGM traces may be too numerous for the physician to easily determine which of the IEGM traces are provided by electrodes in contact with the tissue, and which are not.

An example of a multielectrode catheter is the Octaray® catheter, with in excess of 48 electrodes, produced by Biosense Webster Inc., of Irvine, Calif., USA. The Octaray includes eight deflectable arms disposed at the distal end of a shaft, with each of the deflectable arms including six electrodes. Some catheters may include more electrodes, for example, but not limited to, 120 electrodes.

In addition to the need to determine electrode contact during mapping discussed above, the physician performing an ablation procedure monitors the contact of electrodes with tissue as effective ablation generally requires sufficient contact between the ablation electrode(s) and the tissue. For small numbers of electrodes, monitoring the contact may be performed by presenting a measure of the contact, such as the impedance seen by an electrode or the force on the electrode, numerically or even graphically. However, as the number of active electrodes used in an ablation procedure increases, it becomes increasingly difficult for the physician to monitor any parameter for the individual electrodes. In the case of electrode contact, this problem is exacerbated by the fact that in most cases as the contact varies, so the parameter measuring the contact also varies.

Embodiments of the present invention solve the above problems during a medical procedure such as a mapping or ablation procedure, by presenting a physician with multiple IEGM traces (e.g., voltage versus time graphs) of signals acquired by electrodes of a catheter, while modifying a visual feature of those traces representing electrical activity sensed by the electrodes that are deemed to be in sufficient contact with the heart tissue. Therefore, the traces of electrodes with sufficient tissue contact are highlighted for easy identification by the physician.

The traces representing electrical activity sensed by the electrodes that are in sufficient contact with the heart tissue are typically modified to be brighter compared to traces representing electrical activity sensed by the electrodes that are not in sufficient contact with the heart tissue. The human eye is very sensitive to changes in brightness. Therefore, the brighter traces allow quicker identification of the relevant IEGM traces by the physician.

In some embodiments, traces representing electrical activity sensed by the electrodes that are in sufficient contact with the heart tissue are typically modified to be a different color compared to traces representing electrical activity sensed by the electrodes that are not in sufficient contact with the heart tissue.

In other embodiments, traces representing electrical activity sensed by the electrodes that are in sufficient contact with the heart tissue are typically modified to be a different color and to be brighter compared to traces representing electrical activity sensed by the electrodes that are not in sufficient contact with the heart tissue.

The physician may then inspect the highlighted signals and analyze those signals to find arrythmia and/or determine which electrodes are in contact with the tissue for ablation purposes.

As non-highlighted traces indicate electrodes without sufficient tissue contact, the physician may use this indication to adjust the position of the catheter to improve tissue contact of the electrodes associated with the non-highlighted traces.

In some embodiments, a fading effect is used to dim the brightness, or return the color, used to highlight a trace associated with an electrode in sufficient contact with the tissue, to the original brightness and/or color (used for traces associated with electrodes not in sufficient tissue contact), after the electrode associated with the trace is no longer in sufficient contact with the tissue. The fading effect may take place over any suitable time window, for example, but not limited to, one to three seconds. The fading effect helps to smooth out brightness and/or color changes that would otherwise occur due to intermittent and/or a varying quality of contact.

In the above discussion, sufficiency of tissue contact is used to decide whether or not to highlight the IEGM traces. A quality of contact may be assessed based on different methods including impedance measurements, force or pressure measurements, or from analysis of IEGM traces, as will now be described in more detail.

In response to signals provided by the catheter, processing circuitry assesses a respective quality of contact of each of the catheter electrodes with the tissue in the heart. Any one of the catheter electrodes may be in full or partial contact with the tissue of the heart. In some cases, any one of the catheter electrodes may be in contact with the tissue via another fluid such as blood of various thicknesses. The quality of contact (full or partial contact, or contact via another liquid) of any one of the catheter electrodes with the tissue may be assessed based on the signals provided by the catheter.

The term "quality of contact" as used in the specification and claims is defined herein as a quantitative indicator of the degree of electrical contact between one of the catheter electrodes and the tissue. The "quality of contact" may be expressed directly, for example in terms a measured electrical impedance, or indirectly, for example in terms of contact force, pressure or IEGM amplitude, as will now be described below in more detail.

In some embodiments, the catheter may provide signals which provide an indication of impedance between the catheter electrodes and body surface electrodes. The indication of the impedance provides an indication of a quality of contact, such that a higher value of impedance between one of the catheter electrodes and the body surface electrodes indicates a higher quality of contact between that catheter electrode and the tissue. A value of impedance may be selected to define a minimum quality of contact considered to represent sufficient contact between any one of the catheter electrodes and the tissue.

In some embodiments, the impedance between one of the catheter electrodes and another one of the electrodes on the catheter may be used as a measure of quality of contact. As disclosed in the '529 patent mentioned in the background section above, it is generally known that impedance through blood is generally lower than impedance through tissue. Accordingly, tissue contact may be assessed by comparing impedance values across a set of electrodes to premeasured impedance values when an electrode is known to be in sufficient contact with tissue and when it is known to be in contact only with blood.

In some embodiments, the method of U.S. Pat. No. 9,168,004 to Gliner, at al., which is herein incorporated by reference, may be used to assess quality of contact using a machine learning based method.

In some embodiments, the catheter may provide signals from force or pressure sensors. The indication of force or pressure provides an indication of a quality of contact, such that a higher value of force or pressure indicates a higher quality of contact between a catheter electrode and the tissue. A value of force or pressure may be selected to define a minimum quality of contact considered to represent sufficient contact between any one of the catheter electrodes and the tissue.

In some embodiments, the generated IEGM traces may be used to assess the quality of contact between any one of the catheter electrodes and the tissue. The maximum amplitude of the IEGM trace associated with one of the catheter electrodes is indicative of the quality of contact between that catheter electrode and the tissue, such that a higher value of the maximum amplitude of the IEGM trace indicates a higher quality of contact between that catheter electrode and the tissue. An amplitude value of the IEGM trace may be selected to define a minimum quality of contact considered to represent sufficient contact between any one of the catheter electrodes and the tissue.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
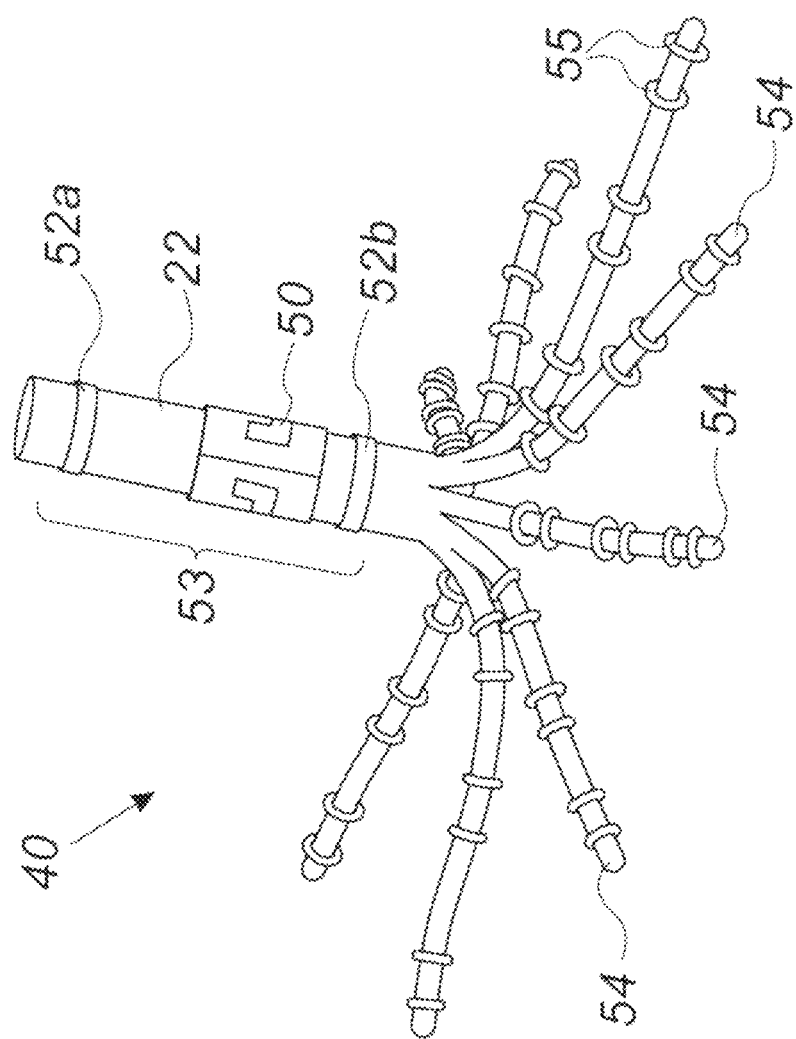
FIG. 2 is a schematic view of a catheter for use in the system of FIG. 1.

Reference is now made to FIG. 1, which is a schematic view of a medical procedure system 20 constructed and operative in accordance with an embodiment of the present invention. Reference is also made to FIG. 2, which is a schematic view of a catheter 40 for use in the system 20 of FIG. 1.

The medical procedure system 20 is used to determine the position of the catheter 40, seen in an inset 25 of FIG. 1 and in more detail in FIG. 2. The catheter 40 includes a shaft 22 and a plurality of deflectable arms 54 (only some labeled for the sake of simplicity) for inserting into a body-part of a living subject. The deflectable arms 54 have respective proximal ends connected to the distal end of the shaft 22.

The catheter 40 includes a position sensor 53 disposed on the shaft 22 in a predefined spatial relation to the proximal ends of the deflectable arms 54. The position sensor 53 may include a magnetic sensor 50 and/or at least one shaft electrode 52. The magnetic sensor 50 may include at least one coil, for example, but not limited to, a dual-axis or a triple axis coil arrangement to provide position data for location and orientation including roll. The catheter 40 includes multiple electrodes 55 (only some are labeled in FIG. 2 for the sake of simplicity) disposed at different, respective locations along each of the deflectable arms 54. Typically, the catheter 40 may be used for mapping electrical activity in a heart of the living subject using the electrodes 55, or for performing any other suitable function in a body-part of a living subject.

The medical procedure system 20 may determine a position and orientation of the shaft 22 of the catheter 40 based on signals provided by the magnetic sensor 50 and/or the shaft electrodes 52 (proximal-electrode 52a and distal-electrode 52b) fitted on the shaft 22, on either side of the magnetic sensor 50. The proximal-electrode 52a, the distal-electrode 52b, the magnetic sensor 50 and at least some of the electrodes 55 are connected by wires running through the shaft 22 via a catheter connector 35 to various driver circuitries in a console 24. In some embodiments, at least two of the electrodes 55 of each of the deflectable arms 54, the shaft electrodes 52, and the magnetic sensor 50 are connected to the driver circuitries in the console 24 via the catheter connector 35. In some embodiments, the distal-electrode 52b and/or the proximal electrode 52a may be omitted.

The illustration shown in FIG. 2 is chosen purely for the sake of conceptual clarity. Other configurations of shaft electrodes 52 and electrodes 55 are possible. Additional functionalities may be included in the position sensor 53. Elements which are not relevant to the disclosed embodiments of the invention, such as irrigation ports, are omitted for the sake of clarity.

A physician 30 navigates the catheter 40 to a target location in a body part (e.g., a heart 26) of a patient 28 by manipulating the shaft 22 using a manipulator 32 near the proximal end of the catheter 40 and/or deflection from a sheath 23. The catheter 40 is inserted through the sheath 23, with the deflectable arms 54 gathered together, and only after the catheter 40 is retracted from the sheath 23, the deflectable arms 54 are able to spread and regain their intended functional shape. By containing deflectable arms 54 together, the sheath 23 also serves to minimize vascular trauma on its way to the target location.

Console 24 comprises processing circuitry 41, typically a general-purpose computer and a suitable front end and interface circuits 44 for generating signals in, and/or receiving signals from, body surface electrodes 49 which are attached by wires running through a cable 39 to the chest and to the back, or any other suitable skin surface, of the patient 28.

Console 24 further comprises a magnetic-sensing subsystem. The patient 28 is placed in a magnetic field generated by a pad containing at least one magnetic field radiator 42, which is driven by a unit 43 disposed in the console 24. The magnetic field radiator(s) 42 is configured to transmit alternating magnetic fields into a region where the body-part (e.g., the heart 26) is located. The magnetic fields generated by the magnetic field radiator(s) 42 generate direction signals in the magnetic sensor 50. The magnetic sensor 50 is configured to detect at least part of the transmitted alternating magnetic fields and provide the direction signals as corresponding electrical inputs to the processing circuitry 41.

In some embodiments, the processing circuitry 41 uses the position-signals received from the shaft electrodes 52, the magnetic sensor 50 and the electrodes 55 to estimate a position of the catheter 40 inside an organ, such as inside a cardiac chamber. In some embodiments, the processing circuitry 41 correlates the position signals received from the electrodes 52, 55 with previously acquired magnetic location-calibrated position signals, to estimate the position of the catheter 40 inside a cardiac chamber. The position coordinates of the shaft electrodes 52 and the electrodes 55 may be determined by the processing circuitry 41 based on, among other inputs, measured impedances, or on proportions of currents distribution, between the electrodes 52, 55 and the body surface electrodes 49. The console 24 drives a display 27, which shows the distal end of the catheter 40 inside the heart 26.

The method of position sensing using current distribution measurements and/or external magnetic fields is implemented in various medical applications, for example, in the Carto® system, produced by Biosense Webster Inc. (Irvine, Calif.), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, issued as U.S. Pat. No. 6,690,963 on Feb. 10, 2004; 2003/0120150 A1, issued as U.S. Pat. No. 7,729,742 on Jun. 1, 2010; and 2004/0068178 A1, now abandoned, whose disclosures are all incorporated herein by reference.

The Carto®3 system applies an Active Current Location (ACL) impedance-based position-tracking method. In some embodiments, using the ACL method, the processing circuitry 41 is configured to create a mapping (e.g., current-position matrix (CPM)) between indications of electrical impedance and positions in a magnetic coordinate frame of the magnetic field radiator(s) 42. The processing circuitry 41 estimates the positions of the shaft electrodes 52 and the electrodes 55 by performing a lookup in the CPM.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

The catheter 40 described above includes eight deflectable arms 54 with six electrodes per arm 54. Any suitable catheter may be used instead of the catheter 40, for example, a catheter with a different number of flexible arms and/or electrodes per arm, or a different probe shape such as a balloon catheter or a lasso catheter, by way of example only.

The medical procedure system 20 may also perform ablation of heart tissue using any suitable catheter, for example using the catheter 40 or a different catheter and any suitable ablation method. The console 24 may include an RF signal generator 34 configured to generate RF power to be applied by an electrode or electrodes of a catheter connected to the console 24, and one or more of the body surface electrodes 49, to ablate a myocardium of the heart 26. The console 24 may include a pump (not shown), which pumps irrigation fluid into an irrigation channel to a distal end of a catheter performing ablation. The catheter performing the ablation may also include temperature sensors (not shown) which are used to measure a temperature of the myocardium during ablation and regulate an ablation power and/or an irrigation rate of the pumping of the irrigation fluid according to the measured temperature.

Figure 3:
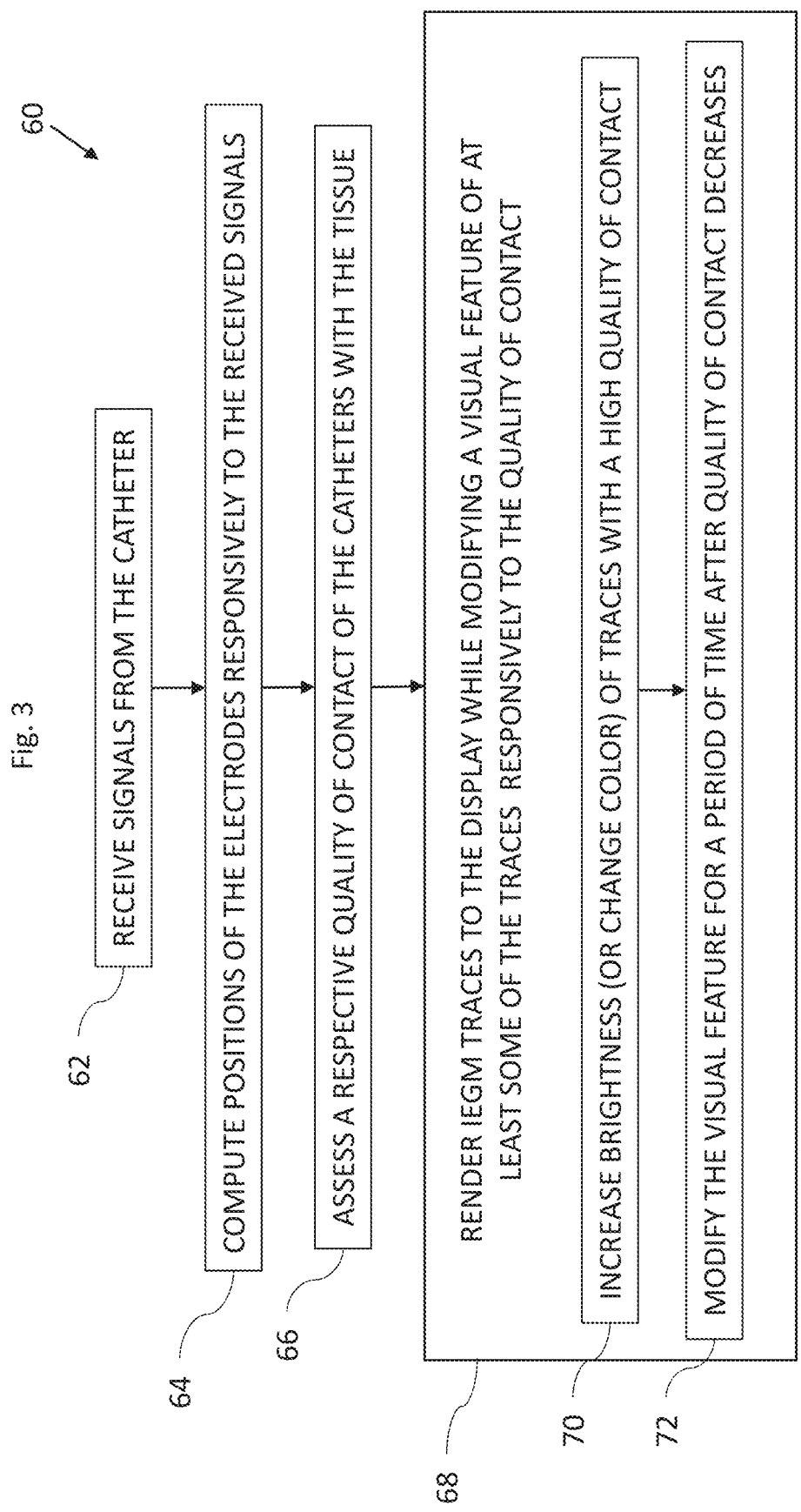
FIG. 3 is a flowchart including exemplary steps in a method of operation of the system of FIG. 1.

Reference is now made to FIG. 3, which is a flowchart 60 including exemplary steps in a method of operation of the system 20 of FIG. 1. Reference is also made to FIGS. 1 and 2.

As previously mentioned, the catheter 40 is configured to be inserted into a chamber of the heart 26 of a living subject (the patient 28). The catheter electrodes 55 are configured to contact tissue at respective locations within the chamber of the heart 26.

The processing circuitry 41 is configured to receive (block 62) signals from the catheter 40. The signals may be received from any of the catheter electrodes 55, the shaft electrodes 52, and/or the magnetic sensor 50 and in some embodiments, from other sensors, such as force or pressure sensors which may provide measurements for use in assessing a quality of contact of the catheter electrodes 55 with the tissue. The signals may also be used to compute positions of the catheter electrodes 55.

The processing circuitry 41 is configured, in response to the signals, to compute (block 64) positions of the catheter electrodes 55. The computation of the positions of the catheter electrodes 55 may be performed based on any suitable position tracking system, for example, based on measured impedances and/or spread of currents, or using the ACL method described above with reference to FIG. 1.

The processing circuitry 41 is configured, in response to the signals, to assess (block 66) a respective quality of contact of each of the catheter electrodes 55 with the tissue in the heart 26. Any one of the catheter electrodes 55 may be in full or partial contact with the tissue of the heart 26. In some cases, any one of the catheter electrodes 55 may be in contact with the tissue via another fluid such as blood of various thicknesses. The quality of contact (full or partial contact, or contact via another liquid) of any one of the catheter electrodes 55 with the tissue may be assessed based on the signals provided by the catheter 40.

As previously mentioned, the term "quality of contact" is a quantitative indicator of the degree of electrical contact between one of the catheter electrodes 55 and the tissue. The "quality of contact" may be expressed directly, for example in terms a measured electrical impedance, or indirectly, for example in terms of contact force, pressure or IEGM amplitude, as will now be described below in more detail.

In some embodiments, the catheter 40 may provide signals which provide an indication of impedance between the catheter electrodes 55 and the body surface electrodes 49, as described in more detail with reference to FIG. 4. The indication of the impedance provides an indication of a quality of contact, such that a higher value of impedance between one of the catheter electrodes 55 and the body surface electrodes 49 indicates a higher quality of contact between that catheter electrode 55 and the tissue. A value of impedance may be selected to define a minimum quality of contact considered to represent sufficient contact between any one of the catheter electrodes 55 and the tissue.

In some embodiments, the impedance between one of the catheter electrodes 55 and another one of the electrodes on the catheter 40 may be used as a measure of quality of contact. As disclosed in the '529 patent mentioned in the background section above, it is generally known that impedance through blood is generally lower than impedance through tissue. Accordingly, tissue contact may be assessed by comparing impedance values across a set of electrodes to premeasured impedance values when an electrode is known to be in sufficient contact with tissue and when it is known to be in contact only with blood.

In some embodiments, the method of U.S. Pat. No. 9,168,004 to Gliner, at al., which is herein incorporated by reference, may be used to assess quality of contact. The '004 Patent describes using machine learning to determine catheter electrode contact. The '004 Patent describes cardiac catheterization being carried out by memorizing a designation of a contact state between an electrode of the probe and the heart wall as an in-contact state or an out-of-contact state, and making a series of determinations of an impedance phase angle of an electrical current passing through the electrode and another electrode, identifying maximum and minimum phase angles in the series, and defining a binary classifier adaptively as midway between the extremes. A test value is compared to the classifier as adjusted by a hysteresis factor, and a change in the contact state is reported when the test value exceeds or falls below the adjusted classifier.

In some embodiments, the catheter 40 may provide signals from force or pressure sensors (not shown), disposed at different locations on the deflectable arms 54, that provide an indication of force or pressure exerted by the catheter electrodes 55 on the tissue. The indication of force or pressure provides an indication of a quality of contact, such that a higher value of force or pressure indicates a higher quality of contact between that catheter electrode 55 and the tissue. A value of force or pressure may be selected to define a minimum quality of contact considered to represent sufficient contact between any one of the catheter electrodes 55 and the tissue. These embodiments, may use any suitable force or pressure sensors as well as any suitable method for measuring the force or pressure, including any of the Patents or Patent Publications mentioned in the background section including the method described in US Patent Publication 2013/0085416, issued as U.S. Pat. No. 10,791,950 on Oct. 6, 2020, of Mest, which is herein incorporated by reference, and describes a method for the in vivo re-calibration of a force sensing probe such as an electrophysiology catheter which provides for the generation of an auto zero zone. The distal tip of the catheter or other probe is placed in a body cavity within the patient. Verification that there is no tissue contact is made using electrocardiogram (ECG) or impedance data, fluoroscopy or other real-time imaging data and/or an electro-anatomical mapping system. Once verification that there is no tissue contact made, the system recalibrates the signal emanating from the force sensor setting it to correspond to a force reading of zero grams and this recalibrated baseline reading is used to generate and display force readings based on force sensor data.

In some embodiments, intracardiac electrogram (IEGM) traces generated by the processing circuitry 41 may be used to assess the quality of contact between any one of the catheter electrodes 55 and the tissue. The maximum amplitude of the IEGM trace associated with one of the catheter electrodes 55 is indicative of the quality of contact between that catheter electrode 55 and the tissue, such that a higher value of the maximum amplitude of the IEGM trace indicates a higher quality of contact between that catheter electrode 55 and the tissue. An amplitude value of the IEGM trace may be selected to define a minimum quality of contact considered to represent sufficient contact between any one of the catheter electrodes 55 and the tissue.

Figure 4:
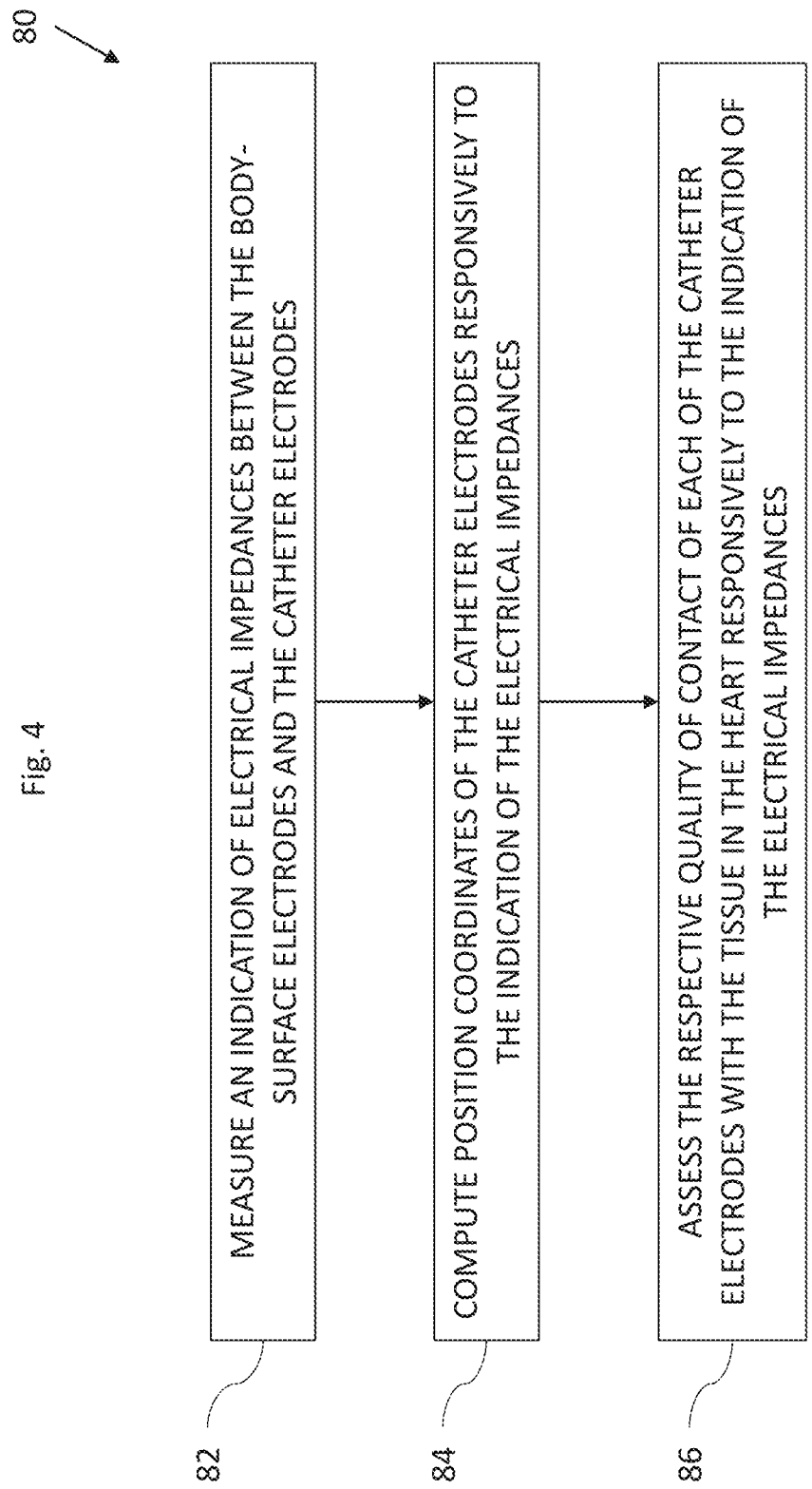
FIG. 4 is a flowchart including exemplary steps in a method of operation of the system of FIG. 1 based on electrical impedances.

Reference is now mad to FIG. 4, which is a flowchart 80 including exemplary steps in a method of operation of the system 20 of FIG. 1 based on electrical impedances. The flowchart 80 includes steps which may be performed instead of, or in addition to, the steps of blocks 64 and 66 of FIG. 3. Reference is also made to FIGS. 1 and 2.

The processing circuitry 41 is configured to measure (block 82) an indication of electrical impedances between the body surface electrodes 49 and the catheter electrodes 55. The processing circuitry 41 is configured to compute (block 84) position coordinates of the catheter electrodes 55 responsively to the indication of the electrical impedances. The computation of the position coordinates may be based on any suitable position tracking method for example, the ACL method described above with reference to FIG. 1, or using measured impedances, or proportions of currents distribution, between the electrodes 55 and the body surface electrodes 49.

The processing circuitry 41 is configured to assess (block 86) the respective quality of contact of each of the catheter electrodes 55 with the tissue in the heart 26 responsively to the indication of the electrical impedances as described in more detail with reference to FIG. 3 hereinabove.

Reference is now made to FIG. 5, which is a schematic view of first exemplary intracardial electrogram (IEGM) traces 88 prepared by the system 20 of FIG. 1. FIG. 5 shows three IEGM traces 88.

The trace 88-1 represents electrical activity in the tissue that is sensed by one of the catheter electrodes 55 (FIG. 2), which has been assessed not to be in sufficient contact with the tissue of the heart 26 (FIG. 1).

The trace 88-2 has been highlighted using a brighter trace than used for the trace 88-1 or a different color than used for the trace 88-1. The trace 88-2 represents electrical activity in the tissue that is sensed by one of the catheter electrodes 55 (FIG. 2), which has been assessed to be in sufficient contact with the tissue.

The trace 88-3 has been partially highlighted (using a brighter trace than that used for the trace 88-1 or a different color than that used for the trace 88-1) in a region 90 corresponding to a first time period when the catheter electrode 55, which sensed the electrical activity represented by the trace 88-3, was assessed to be in sufficient contact with the tissue. After the first time period of sufficient contact, the catheter electrode 55 was not in sufficient contact with the tissue. A fading effect is used in a region 92 of the trace 88-3, corresponding to a second time period after the first time period. The fading effect is used to dim the brightness, or return the color, used to highlight the trace 88-3 in region 90, to the original brightness and/or color (used for traces associated with electrodes not in sufficient tissue contact), after the electrode 55 associated with the trace 88-3 is no longer in sufficient contact with the tissue. The fading effect may take place over any suitable time window, for example, but not limited to, one to three seconds. The fading effect helps to smooth out brightness and/or color changes that would otherwise occur due to intermittent and/or a varying quality of contact.

Reference is now made to FIG. 6, which is a schematic view of second exemplary intracardial electrogram (IEGM) traces 88 prepared by the system 20 of FIG. 1. FIG. 6 shows traces 88 representing electrical activity sensed by about 42 of the catheter electrodes 55. It can be seen that identifying the catheter electrodes 55 in sufficient contact with the tissue from the traces 88 without using trace highlighting would be a very difficult, if not, impossible, task for the physician 30 (FIG. 1) to perform. FIG. 6 shows that four of the traces 88 (labeled 88-4) have been highlighted using a brighter format and/or different color compared to the other non-highlighted traces 88 for easier identification. The traces 88 may be displayed on the display 27 (FIG. 1) with text indicating which of the traces 88 corresponds to which of the catheter electrodes 55 by using some suitable identification for each of the catheter electrodes 55. For example, the trace 88 corresponding to a fifth catheter electrode 55 on a first one of the deflectable arms 54 may be labeled "A5", and the trace 88 corresponding to a first catheter electrode 55 on a third one of the deflectable arms 54 may be labeled "C1".

Reference is again made to FIG. 3. Reference is also made to FIGS. 1 and 2. The processing circuitry 41 is configured, in response to the signals received from the catheter 40, to render (block 68) to the display 27 respective intracardiac electrograms (IEGM) traces 88 representing electrical activity in the tissue that is sensed by the catheter electrodes 55 at respective locations, while modifying a visual feature of at least some of the traces (e.g., traces 88-4 of FIG. 6) responsively to the respective quality of contact of the catheter electrodes 55 with the tissue of the heart 26 at the respective locations. In some embodiments, the processing circuitry 41 is configured to modify the visual feature of the traces (e.g., traces 88-4 of FIG. 6) representing the electrical activity sensed by ones of the catheter electrodes 55 having a quality of contact with the tissue greater than a predefined threshold quality of contact. The predefined threshold quality of contact may be defined with respect to any one or more of the following by way of example only: a predefined impedance, a predefined force, a predefined pressure, and/or a predefined IEGM amplitude, as described above.

In some embodiments, the processing circuitry 41 is configured to modify the visual feature by increasing (block 70) a brightness of at least some of the traces 88 responsively to the respective quality of contact of the catheter electrodes 55 with the tissue of the heart at the respective locations. In some embodiments, the processing circuitry is configured to increase the brightness of the traces (e.g., traces 88-4 of FIG. 6) representing the electrical activity sensed by first ones of the catheter electrodes 55 having a high quality of contact with the tissue relative to the traces 88 representing the electrical activity sensed by second ones of the catheter electrodes having a lower quality of contact with the tissue.

In some embodiments, in addition to, or instead of increasing the brightness of at least some of the traces 88, the processing circuitry 41 is configured to change a color of at least some of the traces 88 responsively to the respective quality of contact of the catheter electrodes 55 with the tissue of the heart 26 at the respective locations. In some embodiments, the processing circuitry 41 is configured to change the color (and optionally increase the brightness) of the traces (e.g., traces 88-4 of FIG. 6) representing the electrical activity sensed by first ones of the catheter electrodes 55 having a high quality of contact with the tissue relative to the traces 88 representing the electrical activity sensed by second ones of the catheter electrodes having a lower quality of contact with the tissue.

As described above with reference to FIG. 5, a fading effect may be used to indicate time periods after electrode contact falls below the predefined threshold quality of contact. The processing circuitry 41 is configured to modify (block 72) the visual feature of the trace(s) 88 for a period of time after the quality of contact decreases below the predefined threshold quality of contact. The step of block 72 is now described in more detail.

Reference is again made to FIG. 5. The processing circuitry 41 (FIG. 1) is configured to perform a first modification (for example, in the region 90) of the visual feature of one of the traces 88-3, for example, representing the electrical activity sensed by one of the catheter electrodes 55 (FIG. 2) having a quality of contact with the tissue greater than the predefined threshold quality during a first time period. The processing circuitry 41 is also configured to perform a second modification or fading effect (for example, in the region 92) of the visual feature of the trace 88-3, for example, representing the electrical activity sensed by that catheter electrode 55 having a quality of contact with the tissue less than the predefined threshold quality during a second time period following the first time period. In some embodiments, the second modification, or fading effect, of the visual feature changes as the second time period progresses. In some embodiments, the second modification, or fading effect, of the visual feature includes the visual feature becoming dimmer (and/or the color of the trace 88-3 reverting to its original color used prior to the first time period) as the second time period progresses.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical system, comprising:
   a catheter configured to be inserted into a chamber of a heart of a living subject, and including catheter electrodes configured to contact tissue at respective locations within the chamber of the heart;
   a display; and
   processing circuitry configured to receive signals from the catheter, and in response to the signals:
   assess a respective quality of contact of each of the catheter electrodes with the tissue in the heart; and
   render to the display respective intracardiac electrograms (IEGM) traces representing electrical activity in the tissue that is sensed by the catheter electrodes at the respective locations, while modifying a visual feature of at least some of the traces responsively to the respective quality of contact of the catheter electrodes with the tissue of the heart at the respective locations indicative of the catheter electrodes making direct contact with the tissue in the heart.

2. The system according to claim 1, wherein the processing circuitry is configured to increase a brightness of at least some of the traces responsively to the respective quality of contact of the catheter electrodes with the tissue of the heart at the respective locations.

3. The system according to claim 2, wherein the processing circuitry is configured to increase the brightness of the traces representing the electrical activity sensed by first ones of the catheter electrodes having a high quality of contact with the tissue relative to the traces representing the electrical activity sensed by second ones of the catheter electrodes having a lower quality of contact with the tissue.

4. The system according to claim 1, wherein the processing circuitry is configured to change a color of at least some of the traces responsively to the respective quality of contact of the catheter electrodes with the tissue of the heart at the respective locations.

5. The system according to claim 4, wherein the processing circuitry is configured to change the color of the traces representing the electrical activity sensed by first ones of the catheter electrodes having a high quality of contact with the tissue relative to the traces representing the electrical activity sensed by second ones of the catheter electrodes having a lower quality of contact with the tissue.

6. The system according to claim 1, wherein the processing circuitry is configured to modify the visual feature of the at least some traces representing the electrical activity sensed by ones of the catheter electrodes having a quality of contact with the tissue greater than a predefined threshold quality of contact.

7. The system according to claim 6, wherein the processing circuitry is configured to:
   perform a first modification of the visual feature of one of the traces representing the electrical activity sensed by one of the catheter electrodes having a quality of contact with the tissue greater than the predefined threshold quality during a first time period; and
   perform a second modification of the visual feature of the one trace representing the electrical activity sensed by the one catheter electrode having a quality of contact with the tissue less than the predefined threshold quality during a second time period following the first time period.

8. The system according to claim 7, wherein the second modification of the visual feature changes as the second time period progresses.

9. The system according to claim 8, wherein the second modification of the visual feature includes the visual feature becoming dimmer as the second time period progresses.

10. The system according to claim 1, further comprising body-surface electrodes configured to be applied to a skin surface of the living subject, wherein the processing circuitry is configured to: measure an indication of electrical impedances between the body-surface electrodes and the catheter electrodes; and compute position coordinates of the catheter electrodes responsively to the indication of the electrical impedances.

11. The system according to claim 10, wherein the processing circuitry is configured to assess the respective quality of contact of each of the catheter electrodes with the tissue in the heart responsively to the indication of the electrical impedances.

12. A medical method, comprising:
   receiving signals from a catheter configured to be inserted into a chamber of a heart of a living subject, and including catheter electrodes configured to contact tissue at respective locations within the chamber of the heart; and
   in response to the signals, assessing a respective quality of contact of each of the catheter electrodes with the tissue in the heart;
   rendering to a display respective intracardiac electrograms (IEGM) traces representing electrical activity in the tissue that is sensed by the catheter electrodes at the respective locations, while modifying a visual feature of at least some of the traces responsively to the respective quality of contact of the catheter electrodes with the tissue of the heart at the respective locations;

performing a first modification of the visual feature of one of the traces representing the electrical activity sensed by one of the catheter electrodes having a quality of contact with the tissue greater than the predefined threshold quality during a first time period; and performing a second modification of the visual feature of the one trace representing the electrical activity sensed by the one catheter electrode having a quality of contact with the tissue less than the predefined threshold quality during a second time period following the first time period, wherein the second modification of the visual feature changes as the second time period progresses via a fading effect.

13. The method according to claim 12, further comprising increasing a brightness of at least some of the traces responsively to the respective quality of contact of the catheter electrodes with the tissue of the heart at the respective locations.

14. The method according to claim 13, wherein the increasing includes increasing the brightness of the traces representing the electrical activity sensed by first ones of the catheter electrodes having a high quality of contact with the tissue relative to the traces representing the electrical activity sensed by second ones of the catheter electrodes having a lower quality of contact with the tissue.

15. The method according to claim 12, further comprising changing a color of at least some of the traces responsively to the respective quality of contact of the catheter electrodes with the tissue of the heart at the respective locations.

16. The method according to claim 15, wherein the changing includes changing the color of the traces representing the electrical activity sensed by first ones of the catheter electrodes having a high quality of contact with the tissue relative to the traces representing the electrical activity sensed by second ones of the catheter electrodes having a lower quality of contact with the tissue.

17. The method according to claim 12, wherein the modifying includes modifying the visual feature of the at least some traces representing the electrical activity sensed by ones of the catheter electrodes having a quality of contact with the tissue greater than a predefined threshold quality of contact.

18. The method according to claim 12, wherein the second modification of the visual feature includes the visual feature becoming dimmer as the second time period progresses.

19. The method according to claim 12, further comprising:

measuring an indication of electrical impedances between body-surface electrodes, configured to be applied to a skin surface of the living subject, and the catheter electrodes; and computing position coordinates of the catheter electrodes responsively to the indication of the electrical impedances.

20. The method according to claim 19, wherein the assessing includes assessing the respective quality of contact of each of the catheter electrodes with the tissue in the heart responsively to the indication of the electrical impedances.

21. A software product, comprising a non-transient computer-readable medium in which program instructions are stored, which instructions, when read by a central processing unit (CPU), cause the CPU to:

receive signals from a catheter configured to be inserted into a chamber of a heart of a living subject, and including catheter electrodes configured to contact tissue at respective locations within the chamber of the heart;

in response to the signals, assess a respective quality of contact of each of the catheter electrodes with the tissue in the heart in order to determine if the catheter electrodes are in direct contact with the tissue in the heart; and render to a display respective intracardiac electrograms (IEGM) traces representing electrical activity in the tissue that is sensed by the catheter electrodes at the respective locations, while modifying a visual feature of at least some of the traces responsively to the respective quality of contact of the catheter electrodes with the tissue of the heart at the respective locations.

22. The software product of claim 21, wherein the visual feature comprises a brightness of the respective intracardiac electrograms (IEGM) traces.

23. The software product of claim 21, wherein the visual feature comprises a color of the respective intracardiac electrograms (IEGM) traces.

* * * * *